United States Patent
Jensen et al.

(10) Patent No.: US 7,282,344 B2
(45) Date of Patent: Oct. 16, 2007

(54) CATION CONDUCTING GABA$_A$ RECEPTORS AND THEIR USE

(75) Inventors: Marianne Lerbech Jensen, Ballerup (DK); Philip K. Ahring, Ballerup (DK); Thomas Varming, Ballerup (DK)

(73) Assignee: Neurosearch A/S, Ballerup (DK)

( * ) Notice: Subject to any disclaimer, the term of this patent is extended or adjusted under 35 U.S.C. 154(b) by 212 days.

(21) Appl. No.: 10/479,251

(22) PCT Filed: Jun. 4, 2002

(86) PCT No.: PCT/DK02/00378

§ 371 (c)(1),
(2), (4) Date: Dec. 1, 2003

(87) PCT Pub. No.: WO02/098907

PCT Pub. Date: Dec. 12, 2002

(65) Prior Publication Data

US 2005/0049190 A1     Mar. 3, 2005

(30) Foreign Application Priority Data

Jun. 6, 2001   (DK) .......................... PA 2001 00881

(51) Int. Cl.
  *C07K 14/705*   (2006.01)
  *G01N 33/53*    (2006.01)
  *G01N 33/60*    (2006.01)
(52) U.S. Cl. ..................... 435/7.21; 530/350
(58) Field of Classification Search ............. None
See application file for complete search history.

(56) References Cited

U.S. PATENT DOCUMENTS 5,468,742 A   11/1995   Petersen et al.
5,659,038 A    8/1997   Himmler et al.

FOREIGN PATENT DOCUMENTS

WO      99/29319 A2    6/1999

OTHER PUBLICATIONS

Kardos 1999. Neurochemistry International 34:353-358.*
Buhr 1997. Proc Natl Acad Sci USA 94:8824-8829.*
Baulac et al. 2001. Nature Genetics 28:46-48.*
Peng 1994. Molecular Pharmacology 45:546-554.*
Kuner 2000. Neuron 27:447-459.*
Jones-Davis 2003. Current Opinion in Pharmacology 3:12-18.*
Bonnert et al. 1999. PNAS 96:9891-9896.*
Gunthorpe Martin J. et al.: Journal of Biological Chemistry, vol. 276, No. 24, (Jun. 15, 2001), pp. 10977-10983, XP002225316.
Angelo Keramidas et al.: Biophysical Journal, vol. 78, (Jul. 2000), pp. 247-259, XP002225317.
Jean-Luc Galzi et al.: NATURE, vol. 359, No. 6395, (1992), pp. 500-505, XP002225318.
Database Biosis [online] : Biosciences Information Service, Philadelphia, PA, US; 2001, Wotring V E et al.: Database accession No. PREV200100481682, XP002225321 (abstract) & Society for Neuroscience Abstract, vol. 27, No. 1, 2001, p. 86, 31$^{st}$ Annual Meeting of the Society for Neuroscience; San Diego, California, USA; (Nov. 10-15, 2001).
Wang Chih-Tien et al.: Biophysical Journal, vol. 77, (Aug. 1999), pp. 691-700, XP002225319.
Marianne L. Jensen et al.: The Journal of Biological Chemistry, vol. 277, No. 44, 2002, pp. 41438-41447, XP002225320.
Database Biosis [online] Biosciences Information Service, Philadelphia, PA, US; (Jan. 2002) Wotring Virginia E. et al.: Database accession No. PREV200200365112, XP002225322 (abstract) & Biophysical Journal, vol. 82, No. 1 part 2, (Jan. 2002), p. 351a, 46$^{th}$ Annual Meeting of the Biophysical, Feb. 23-27, 2002 (Jan. 2002).
D. Bertrand et al.: NEUROBIOLOGY, Proc. Natl. Acad. Sci., vol. 90 pp. 6971-6975, (1993).
Marianne L. Jensen et al., "A cation conducting GABA$_A$ receptor", Abstract of an oral presentation made at a meeting on Jun. 7, 2001 in Sandbjerg, Denmark.
Jensen, et al., "Mutational Studies Using a Cation-Conducting GABA$_A$ Receptor Reveal the Selectivity Determinants of the Cys-Loop Family of Ligand-Gated Ion Channels", Journal of Neurochemistry, vol. 92, pp. 962-972, 2005.
Martin, et al., "GABA Receptors", Tocris Reviews, No. 20, pp. 1-8, Mar. 2002.
C. Miller, "Genetic Manipulation of Ion Channels: A New Approach to Structure and Mechanism", Neuron, vol. 2, pp. 1195-1205, Mar. 1989.

* cited by examiner

*Primary Examiner*—Robert C. Hayes
*Assistant Examiner*—Daniel E. Kolker
(74) *Attorney, Agent, or Firm*—Birch, Stewart, Kolasch & Birch, LLP

(57) ABSTRACT

This invention relates to cation conducting GABA$_A$ receptors, mutated GABA$_A$ receptor subunits, polynucleotide sequences encoding mutated subunits, expression vectors comprising the mutated subunits, host cells capable of expressing the mutated subunits, drug screening methods, and chemical substances identified by the drug screening methods of the invention.

14 Claims, No Drawings

CATION CONDUCTING $GABA_A$ RECEPTORS AND THEIR USE

TECHNICAL FIELD

This invention relates to cation conducting $GABA_A$ receptors, mutated $GABA_A$ receptor subunits, polynucleotide sequences encoding mutated subunits, expression vectors comprising the mutated subunits, host cells capable of expressing the mutated subunits, drug screening methods, and chemical substances identified by the drug screening methods of the invention.

BACKGROUND ART

Preferred drug screening method of ion channels include the standard high throughput screens (HTS) using mixtures of test compounds and biological reagents along with indicator compound loaded into cells in arrays of wells, usually in standard microtiter plates with 96 or 384 wells, and measuring the signal from each well, either fluorescence emission, intracellular pH, optical density, radioactivity, etc.

The $GABA_A$ receptor is an attractive target for the development of new drugs. The $GABA_A$ receptor, however, is a chloride channel, rendering it incompatible with conventional HTS methods. Moreover, most cells capable of functionally expressing $GABA_A$ receptors do not maintain a sufficient chloride gradient across their membranes. For validating these targets, cost and time-consuming electrophysiological methods are still the preferred methods.

There is a strong felt need in the art to make these receptors the target for more efficient and inexpensive high throughput drug screening methods.

Wang et al. [Wang Chih-Tien et al: Cation Permeability and Cation-Anion Interactions in a Mutant GABA-Gated Chloride Channel from *Drosophila; Biophys. J.* 1999 77 691-700] describe an insect GABA receptor that has been made cation permeable by mutation in the near-M2 region. This receptor, however, does not contain modulator sites affected by drugs, and is not suited for high throughput drug screening.

Bertrand et al. [Bertrand D, Galzi J L, Devillers-Thieiy A, Bertrand S & Changeux J P: Mutations at two distinct sites within the channel domain M2 alter calcium permeability of neuronal $\alpha 7$ nicotinic receptor; *Proc. Natl. Acad. Sci. USA* 1993 90 6971-6975] describe how mutations at two distinct sites within its TM2 domain alter the calcium permeability of a nicotinic $\alpha 7$ receptor.

Keramidas et al. [Keramidas A, Moorhouse A J, French C R, Schofield P R & Barry P H. M2 Pore Mutations Convert the Glycine Receptor Channel from Being Anion- to Cation-Selective; *Biophys. J.* 2000 78 247-259] describe how three mutations carried out in the M2 transmembrane domain of the chloride-conducting $\alpha 1$ homomeric glycine receptor alter the receptor from being anion- to cation-selective.

A cation-conducting $GABA_A$ receptor suited for high throughput drug screening has never been disclosed.

SUMMARY OF THE INVENTION

It is an object of the present invention to provide a cabon-conducting human $GABA_A$ receptor that is suited for high throughput drug screening.

Accordingly, in its first aspect, the invention provides a cation-conducting human $GABA_A$ receptor.

In another aspect the invention provides mutated $GABA_A$ receptor subunits, comprising one or more mutations in the loop bridging its first and second transmembrane domain (TM1 and TM2).

In yet another aspect the invention relates to polynucleotide sequences encoding the mutated subunit of the invention.

In a fourth aspect the invention provides expression vectors comprising the polynucleotide sequence of the invention.

In a fifth aspect the invention provides host cells comprising the polynucleotide sequence of the invention, or the expression vector of the invention.

In a sixth aspect the invention provides methods of screening chemical compounds for inhibiting, activating or modulating activity of a cation-conducting $GABA_A$ receptor, which method comprises the steps of (i) subjecting a cation-conducting $GABA_A$ receptor containing cell to the action of the chemical compound to be screened;

(ii) subjecting the cation-conducting $GABA_A$ receptor containing cell to activation with GABA or any other GABA-acting substance; and (iii) monitoring ion flux through the cation-conducting $GABA_A$ receptor, either directly or indirectly, and thereby determining the action of the chemical compound.

In a final aspect the invention relates to the chemical compounds identified by the method of the invention, and to the use of such compounds for diagnosis, treatment, prevention or alleviation of a disease or a disorder or a condition of a mammal, including a human, which disease, disorder or condition is related to $GABA_A$ receptor dysfunction.

Other objects of the invention will be apparent to the person skilled in the art from the following detailed description and examples.

DETAILED DISCLOSURE OF THE INVENTION

The present invention relates to and provides cation-conducting human $GABA_A$ receptors.

The $GABA_A$ receptor is the major inhibitory receptor of the central nervous system and is composed of five subunits that assemble to form a chloride channel. To date six main types of $GABA_A$ receptor subunits have been described, the $\alpha$ subunit (of which six have been described, i.e. $\alpha 1$-6), the $\beta$ subunit (of which three have been described, i.e. $\beta 1$-3), the $\gamma$ subunit (of which three have been described, i.e. $\gamma 1$-3), the $\delta$ subunit, the $\rho$ subunit ($\rho 1$-3), the $\epsilon$ subunit and the $\theta$ subunit. Wild type (wt) $GABA_A$ receptors are thought consisting primarily of 2 $\alpha$-, 2 $\beta$- and 1 $\gamma$-subunit, but other combinations are also functional, for instance receptors composed only of $\alpha$ and $\beta$ subunits.

Each $GABA_A$ receptor subunit is composed of a large extracellular N-terminal domain, four membrane-spanning domains (TM1-TM4), a small intracellular loop between TM1 and TM2, a small extracellular loop between TM2 and TM3, a large intracellular loop between TM3 and TM4 and a short C-terminal domain. The TM2 domain of each of the five subunits demarcates the chloride-conducting pore of the receptor complex.

According to the present invention it has now been found that a set of mutations introduced in the intracellular loop bridging TM1 and TM2 transmembrane domain, and/or in TM2 itself, affect the physiology of the mutated receptor in a way that the receptor is no longer conducting chloride ions, but rather cations, thereby constituting a cation-conducting GABA$_A$ receptor.

In describing the present invention, amino acids are designated using the established one-letter symbols.

Cation-Conducting GABA$_A$ Receptors

In its first aspect the invention provides a cation-conducting human GABA$_A$ receptor. More specifically the cation-conducting GABA$_A$ receptor of the invention may be characterised as being a functional derivative of a wild-type GABA$_A$ receptor, derived from the wild-type GABA$_A$ receptor by mutation, and thus being a mutated GABA$_A$ receptor.

In a preferred embodiment the cation-conducting GABA$_A$ receptor of the invention comprises at least one mutated subunit, which subunit holds one or more mutations in the loop bridging its first and its second transmembrane domain (TM1 and TM2), and/or even in the TM2 domain itself.

In a more preferred embodiment the cation-conducting GABA$_A$ receptor of the invention comprises at least one mutated α subunit, and/or at least one mutated β subunit, and/or at least one mutated γ subunit. In an even more preferred embodiment the subunit is a mutated α1, α2, α3, α4, α5, α6, β1, β2, β3, γ1 γ2, and/or γ3 subunit.

Mutated GABA$_A$ Receptor Subunits

In another aspect the invention provides a mutated GABA$_A$ receptor subunit comprising one or more mutations in the loop bridging its first and second transmembrane domain (TM1 and TM2), and/or even in the second transmembrane domain (TM2). The mutated GABA$_A$ receptor subunit of the invention may be characterised as being a functional derivative of a wild-type GABA$_A$ receptor subunit, derived from the wild-type GABA$_A$ receptor subunit by mutation, and thus being a mutated GABA$_A$ receptor subunit.

The mutated GABA$_A$ receptor subunit of the invention may in particular be a mutated α1, α2, α3, α4, α5, α6, β1, β2, β3, γ1 γ2 or γ3 subunit.

In a preferred embodiment the mutation contemplated according to the present invention should be introduced
- at positions corresponding to the position of the partial amino acid sequence represented by "ESVPAR" (SEQ ID NO: 14) in the wild-type GABA$_A$ receptor α subunits,
- at positions corresponding to the position of the partial amino acid sequence represented by "DASAAJR" (SEQ ID NO: 15) in the wild-type GABA$_A$ receptor β subunits, or
- at positions corresponding to the position of the partial amino acid sequence represented by "DAVPAR" (SEQ ID NO: 16) in the wild-type GABAA receptor γ subunits,
- i.e. at amino acid positions–6' to–1' when numbered according to TM2.

In a more preferred embodiment above-identified partial 6 amino acid sequence is substituted for the partial 5 amino acid sequence DSGEK (SEQ ID NO: 17), or any subsequence thereof or any conservative substitution thereof, in the ioop bridging its first and its second transmembrane domain (TM1 and TM2). Expressed another way, the above-identified partial 6 amino acid sequence is substituted for the following partial 5 amino acid sequence:

$X^1X^2X^3X^4X^5$ (SEQ ID NO: 18);

wherein
$X^1$ designates D or E;
$X^2$
$X^3$ designates S. C or A;
$X^3$ designates G, A or V;
$X^4$ designates E or D; and
$X^5$ designates K or R.

Most preferred mutants of the invention holds a partial amino acid sequence selected from the following list (SEQ ID NOS: 19-54)

```
DSGEK, DSGDK, DSAEK, DSADK, DSVEK, DSVDK,
DCGEK, DCGDK, DCAEK, DCADK, DCVEK, DCVDK,
DAGEK, DAGDK, DAAEK, DAADK, DAVEK, DAVDK,
DSGER, DSGDR, DSAER, DSADR, DSVER, DSVDR,
DCGER, DCGDR, DCAER, DCADR, DCVER, DCVDR,
DAGER, DAGDR, DAAER, DAADR, DAVER, DAVDR.
```

Polynucleotide Sequences Encoding Mutated Subunits

In another aspect the invention provides a purified and isolated polynucleotide sequence encoding the mutated GABA$_A$ receptor subunit of the invention. The mutated GABA$_A$ receptor subunit encoded by the polynucleotide sequence of the invention may in particular be a mutated α1, α2, α3, α4, α5, α6, β3, β2, β3, γ1 γ2 or γ3 subunit.

Recombinant Expression Vectors

In a further aspect the invention provides a recombinant expression vector comprising the polynucleotide of the invention.

As defined herein, a recombinant expression vector is an expression vehicle or recombinant expression construct used for introducing polynucleotides into a desired cell. The expression vector may be a virus vector or a plasmid vector, in which the polynucleotide of the invention may be inserted. Suitable expression vehicles include, but are not limited to eukaryotic expression vectors and prokaryotic expression vectors, e.g. bacterial linear or circular plasmids, and viral vectors. However, any other plasmid or vector may be used as long as they are replicable and viable in the production host.

Preferred eukaryotic expression vectors include pWL-NEO, pSV2CAT, pOG44, pXT1, pSG (available from Stratagene); pSVK3, pBPV, pMSG, pSVL (available from Pharmacia); and pcDNA-3 (available from Invitrogen).

The expression vector may further comprise regulatory sequences in operable combination with the polynucleotide sequence of the invention. As defined herein, the term "in operable combination" means that the operable elements, i.e. gene(s) and the regulatory sequences, are operably linked so as to effect the desired expression.

Host Cells

In a yet further aspect the invention provides a host cell comprising the solated polynucleotide sequence of the invention, and/or or a recombinant expression vector of the invention.

The production cell of the invention preferably does not express, or is avoid any endogen GABA$_A$ subunit activity.

The production cell of the invention may preferably be a eukaryotic cell, in particular a human cell, or a fungal cell, such as a yeast cell or a filamentous fungal cell. Preferred cells include HEK293, CHO-k1, BHK, COS7, PC12, HiB5, RN33b cell, and a *Xenopus laevis* oocyte (XLO), or any other cell line able to express the cation-conducting GABA$_A$ receptor of the invention.

Methods of Drug Screening

The cation-conducting $GABA_A$ receptor of the invention allows for the first time the drug screening process to be carried out using conventional high-throughput screening technologies.

Therefore, in another aspect the invention provides a method for the screening of chemical compounds for $GABA_A$ receptor activity, by which method a chemical compound having $GABA_A$ receptor activity is identified by its ability to inhibit, activate or modulate the flux of ions through the $GABA_A$ receptor, to change the intracellular pH, or to change the membrane potential of a cation-conducting $GABA_A$ receptor containing cell.

In a preferred embodiment the method of the invention comprises the steps of
  (i) subjecting a cation-conducting $GABA_A$ receptor containing cell to the action of the chemical compound to be screened;
  (ii) subjecting the cation-conducting $GABA_A$ receptor containing cell to activation with GABA or any other GABA-acting substance; and
  (iii) monitoring ion flux through the cation-conducting $GABA_A$ receptor, either directly or indirectly, thereby determining the action of the chemical compound.

The Cation-Conducting $GABA_A$ Receptor Containing Cell

The cation-conducting $GABA_A$ receptor containing cell used in the method of the invention preferably is a host cell of the invention as described above.

Monitoring of the Ion Flux

According to the method of the invention, the ion flux through the cation-conducting $GABA_A$ receptor is monitored in order to determine inhibition, activation or modulation of ion flux caused by the chemical compound. The ion flux may be monitored directly or indirectly using established methods.

In a preferred embodiment monitoring of the flux through the cation-conducting $GABA_A$ receptor is performed using fluorescence or radio-ligand methods.

In a more preferred embodiment the cabon-conducting $GABA_A$ receptor containing cell is loaded or incubated with a fluorescence dye or radio-ligand that allows for a determination of changes in ion flux through the cation-conducting $GABA_A$ receptor caused by the addition of the chemical test substance and GABA or the GABA-acting compound.

Preferred fluorescence indicators include, but are not limited to FLUO-3, FLUO4, Calcium Green, FURA-2, SBFl, PBFl, CD222, and BCECF, $DIBAC_4(3)$, $DiOC5(3)$, and $DiOC2(3)$.

Preferred radioligands include, but are not limited to $Rb^+$ and organic cations such as $TPP^+$.

In yet another preferred embodiment monitoring of ion flux through the cation-conducting $GABA_A$ receptor may be performed by spectroscopic methods, e.g. using a FLIPR assay (Fluorescence Image Plate Reader; available from Molecular Devices), or by using the automated analysis equipment described in U.S. Pat. No. 5,670,113.

In yet another preferred embodiment monitoring of the ion flux through the cation-conducting $GABA_A$ receptor is performed by patch clamp techniques, e.g. as described by Hamill, O. P., et al., *Pflüigers Arch.* 1981 351 85-100. In a more preferred embodiment, monitoring of the membrane potential of the cation-conducting $GABA_A$ receptor containing cell is performed by the automatic patch clamp method described in WO 98/50791.

Cation-Conducting $GABA_A$ Receptor Active Compounds

In another aspect the invention relates to chemical compounds identified by the method of the invention, and capable of inhibiting, activating or modulating $GABA_A$ receptors.

The chemical compounds of the invention are useful for the diagnosis, treatment, prevention or alleviation of a disease or a disorder or a condition of a mammal, including a human, which disease, disorder or condition is related to $GABA_A$ receptor dysfunction. In a preferred embodiment, the disease, disorder or condition is asthma, acute heart failure, hypotension, urinary retention, osteoporosis, hypertension, angina pectoris, myocardial infarction, ulcers, allergies, benign prostatic hypertrophy, prostate cancer, Parkinson's disease, psychotic and neurological disorders, anxiety, schizophrenia, mania, depression, dyskinesia, memory disorders, sleep disorders, convulsive disorders, and epilepsy.

EXAMPLES

The invention is further illustrated with reference to the following examples, which are not intended to be in any way limiting to the scope of the invention as claimed.

Example 1

Mutagenesis and Expression of Mutated Receptors

To investigate the influence of the $GABA_A$ receptor subunits in defining the ion selectivity of the receptor, a mutant $GABA_A$ receptor subunit $\beta_3$ was designed by site directed mutagenesis.

The $GABA_A$ receptor subunits were cloned by RT-PCR from human brain mRNA (Clontech). The $GABA_A$ receptor α subunit was sub-cloned into the pNS1z vector, the $GABA_A$ receptor β subunit was sub-cloned into the pNS1n vector, and the $GABA_A$ receptor γ subunit was sub-cloned into the pZeoSV vector (Invitrogen). pNS1n and pNS1z were derived from pcDNA3-Neo (Invitrogen) or pcDNA3-Zeo (Invitrogen), respectively.

A hindIII site was introduced in the loop between the M1 and M2 domains and a bsu36I site was introduced in the loop between the M2 and M3 domains in all receptor subunits. hindIII and bsu36I sites at other positions within the vectors or cDNAs were eliminated.

A set of chimeric $GABA_AR$ subunits was constructed in which the M2 domain was moved from one subunit to another by simple restriction digestion and ligation. The $GABA_AR$ encoding plasmids were digested by the restriction enzymes hindIII and bsu36I, and fragments were then separated using gel-electrophoresis and purified using a gel extraction kit (Qiagen). Chimeric $GABA_AR$ subunits were obtained by ligation of the fragments using the rapid ligation kit (Roche).

To create chimeric $GABA_ARs$ with non-GABA M2 domains, overlapping oligonucleotides encoding the entire M2 domains were annealed and elongated using Expand DNA polymerase.

The elongation conditions were as follows: 94° C. for 2 minutes, followed by 20 cycles of 94° C. for 1 minute, 59° C. for 1 minute and 72° C. for 1 minute, and ending with an incubation at 72° C. for 10 minutes. The synthetic M2 domains were digested with hindIII and bsiB6I and ligated with the cDNA of a $GABA_AR$ subunit.

Mutations were introduced into the cDNA's of the $GABA_A$ receptor $\beta_3$ subunit using the QUANT-ESSENTIAL SDM kit (Quantum Biotechnologies). A block of 6 amino acids (DASAAR) (SEQ ID NO: 15) at the TM2 border of the β$_3$ subunit was replaced by the corresponding amino acids of the AChRα$_7$ (DSGEK) (SEQ ID NO: 19).

The mutagenesis was performed using the following oligonucleotide primers:

hGABA α$_2$ -E s

5' AGTAAGCTTC TGGCTTAACA GAGAATCTGT GGAGCGTACG   (SEQ ID NO: 1)

GTGTTTGGAG TCACCACTGT CCTGAC 3' hGABA α$_2$ DSG-EK s

5' AGTAAGCTTC TGGCTTAACA GAGACTCCGG CGAGAAGACT   (SEQ ID NO: 2)

GTGTTTGGAG TCACCACTGT CCTGAC 3' hGABA α$_2$ M2 as

5' CCACCTTAGG GAGAGAATTC CGAGCACTGA TGCTTAGAGT   (SEQ ID NO: 3)

TGTCATTGTC AGGACAGTGG TG 3' hGABA β$_3$ -E s

5' GGTAAGCTTC TGGATCAATT ATGATGCATC TGAACGCGTT   (SEQ ID NO: 4)

GCCCTCGGGA TCACCACTGT CCTGAC 3' hGABA β$_3$ SG-EK s

5' GTAAGCTTCT GGATCAATTA TGACTCCGGC GAGAAGGTTG   (SEQ ID NO: 5)

CCCTCGGGAT CACCACTGTC CTGAC 3' hGABA β$_3$ M2 as

5' GGACCTTAGG CAAGGTCTCC CGAAGGTGGG TGTTGATGGT   (SEQ ID NO: 6)

TGTCATTGTC AGGACAGTGG TG 3' hGABA γ$_2$ -E s

5' GGTAAGCTTC TGGATCAATA AGGATGCTGT TGAGCGTACG   (SEQ ID NO: 7)

TCTTTAGGTA TCACCACTGT CCTGAC 3' hGABA γ$_2$ SG-EK s

5' GGTAAGCTTC TGGATCAATA AGGACTCCGG CGAGAAGACA   (SEQ ID NO: 8)

TCTTTAGGTA TCACCACTGT CCTGAC 3' hGABA γ$_2$ M2 as

5' AGACCTTAGG GAGCGATTTC CGGGCAATGG TGCTGAGGGT   (SEQ ID NO: 9)

GGTCATTGTC AGGACAGTGG TG 3'

To create further mutated GABA$_A$R β$_3$ subunits the following oligonucleotide primers were used:

hGABA β$_3$ SG-E s

5' GACTCGGGCG AGAGAGTTGC CCTCGGGATC 3'           (SEQ ID NO: 10)

hGABA β$_3$ G-EK s

5' CTGGATCAAT TATGACGCAG GCGAGAAGGT TGCC 3'     (SEQ ID NO: 11)

hGABA β$_3$ G-E s

5' CTGGATCAAT TATGACGCAG GCGAGAGAGT TGCCCTCGGG ATC   (SEQ ID NO: 12)
3'

Introduction of the bsu36I site in the hGABA$_A$R β$_3$ subunit led to the I300V mutation, which turned out to affect receptor function. This was reversed using the following oligonucleotide primer:

hGABA β$_3$ V300I

5' GAGACCTTGC CTAAGATCCC     (SEQ ID NO: 13)
CTATGTCAAA GCC 3'

Correct mutagenesis was verified by restriction enzyme analysis and by DNA sequencing. CHO-k1 cells (ATCC) were co-transfected with the plasmids described above and a plasmid encoding enhanced green fluorescent protein (GFP, Clontech), using the lipofectamine PLUS kit (Life Technologies).

Example 2

Expression of Mutated Receptors

All constructs were expressed in CHO-K1 cells (ATCC No. CCL61).

CHO-KL cells were maintained in DMEM with 10 mM HEPES and 2 mM glutamax supplemented with 10% fetal bovine serum and 2 mM L-proline (Life Technologies). The cells were cultured at 37° C. in a humidified atmosphere of 5% CO$_2$ and 95% air and passaged twice a week.

CHO-K1 cells were co-transfected with the plasmids described above and a plasmid encoding enhanced green fluorescent protein using the lipofectamine PLUS kit (Life Technologies) according to manufacturers protocol.

Binding experiments and electrophysiological measurements were performed 24-48 hours after transfection.

Example 3

Binding Assays

Binding studies were performed using standard methods. Membranes were prepared from CHO-K1 cells expressing recombinant GABA$_A$R subunits. The cells were washed in PBS (Life Technologies), trypsinized, washed twice in tris-citrate buffer (50 mM, pH 7.1) and centrifuged for 10 minutes at 5,000 g.

[$^3$H]-Muscimol Binding

Membranes were resuspended in membrane wash buffer [20 mM KH$_2$PO$_4$K$_2$HPO$_4$, pH 7.5, 50 mM KCl, 0.025% (w/v) NaN$_3$, and various protease inhibitors (1 mM EDTA, 2 mM benzamidine chloride, 0.1 mM benzethonium chloride, 50 U/ml bacitracin, 0.3 mM phenylmethylsulfonyl fluoride, 10 mg/l ovomucoid trypsin inhibitor, 10 mg/l soybean trypsin inhibitor)] and centrifuged for 30 minutes at 177,000 g and 4° C. The pellet was resuspended in binding assay buffer (20 mM KH$_2$PO$_4$/K$_2$HPO$_4$, pH 7.5 and 100 mM KCl) to a protein concentration of 1 mg/ml and homogenized just before use. Binding was performed with 1, 3, 10, 30, 100 or 300 nM of [$^3$H]-muscimol (20 Ci/mmol, Dupont-New England Nuclear) in triplicate in a final volume of 250 μl containing 200 μg of protein, and non-specific binding was determined in the presence of 1 mM GABA (Sigma). Samples were incubated at 4° C. for 30 minutes and labelled membranes were harvested on a Brandel cell harvester using GF/B filters (Whatman). The filters were washed with 3×4 ml binding assay buffer and the amount of radioactivity was determined by liquid scintillation counting.

[$^3$H]-Flumazenil Binding

Membranes were resuspended in tris-citrate buffer and centrifuged for 10 minutes at 22,000 g at 4° C. The pellet was resuspended in tris-citrate buffer to a protein concentration of 100-200 μg/ml. Binding was performed with 0.5, 1, 2, 3 or 6 nM [$^3$H]-flumazenil (87 Ci/mmol, Dupont-New England Nuclear) in triplicate in a final volume of 550 μl containing 50-100 μg protein, and non-specific binding was determined in the presence of 1 μM clonazepam (Roche). Samples were incubated at 4° C. for 40 minutes and labelled membranes were harvested using rapid filtration over GF/C filters (Whatman). The filters were washed with 2×5 ml tris-citrate buffer and the amount of radioactivity was determined by liquid scintillation counting.

[$^{35}$S]-TBPS Binding

Membranes were resuspended in tris-citrate buffer and centrifuged for 10 minutes at 22,000 g at 4° C. The pellet was resuspended in 20 mM KH$_2$PO$_4$ buffer (pH 7.4) containing 200 mM KCl to a protein concentration of 200-400 μg/ml. Binding was performed in triplicate with 5 nM [$^{35}$S]-TBPS (89 Ci/mmol, Dupont-New England Nuclear) and 0.6 μM GABA in a final volume of 550 μl containing 100-200 μg of protein, and non-specific binding was determined in the presence of 200 μM picrotoxin (Sigma). Samples were incubated at 20-220° C. for 150 minutes and binding was terminated by rapid filtration over Whatman GF/C filters. The filters were washed with 2×5 ml 20 mM KH$_2$PO$_4$ buffer (pH 7.4) containing 200 mM KCl and the amount of radioactivity was determined by liquid scintillation counting.

(+) indicates more and (÷) indicates less than 2.5% binding of the wt receptor.

Data Analysis

K$_d$ and B$_{max}$ were estimated using a one site binding equation.

The results of this experiment are presented in Table 1, below.

Example 4

Characterisation

The mutant GABA$_A$ receptor subunit β3 obtained according to Examples 1-2 was characterized electrophysiologically with respect to reversal potentials.

All experiments were performed in voltage clamp using conventional whole cell patch clamp methods. The amplifier was an EPC-9 (HEKA-electronics, Lambrect, Germany) run by a Macintosh G3 computer via an ITC-16 interface. Experimental conditions were set with the Pulse-software accompanying the amplifier. Data were low pass filtered and sampled directly to a hard disk at a rate of 3 times the cut-off frequency.

Pipettes were pulled from borosilicate glass (Modulohm) using a horizontal electrode puller (Zeitz-Instrumente). The pipette resistances were 1.6-2.6 mΩ and the pipettes were filled with a solution containing 120 mM KCl 2 mM $MgCl_2$, 10 mM EGTA and 10 mM HEPES adjusted to pH=7.2. The pipette electrode was a chloridized silver wire, and the reference was a silverchloride pellet electrode (In Vivo Metric) fixed to the experimental chamber. The electrodes were zeroed with the open pipette in the bath just prior to sealing. Coverslips with cultured cells were transferred to a 15 µl experimental chamber mounted on the stage of an inverted microscope (IMT-2, Olympus) supplied with Nomarski optics and a mercury lamp (Olympus). Cells chosen for experiments emitted bright green fluorescence when exposed to UV-light from the mercury lamp. After giga-seal formation the whole cell configuration was attained by suction.

Cells were continuously superfused at a rate of 2.5 ml/min with an extracellular solution containing 140 mM NaCl, 4 mM KCl, 2 mM $CaCl_2$, 1 mM $MgCl_2$ and 10 mM HEPES adjusted to pH=7.4. A low chloride extracellular solution (Gluconate-R) containing 5 mM NaCl, 4 mM KCl, 2 mM $CaCl_2$, 1 mM $MgCl_2$, 135 mM NaGluconate and 10 mM HEPES adjusted to pH=7.4 was used to address the chloride permeability and a low sodium extracellular solution (NMDG-R) containing 14 mM NaCl, 4 mM KCl, 2 mM $CaCl_2$, 1 mM $MgCl_2$, 126 mM NMDG and 10 mM HEPES adjusted to pH=7.4 with HCl was used to address the cation permeability.

The cells were held at a holding potential of −60 mV at the start of each experiment and the current was continuously measured for 30 sec to ensure a stable baseline. The I-V experiments were performed by holding the cells at potentials of −60, −50, −40, −30, −20, −10, 0, 10, 20, 30, 40, 50, 60 mV and recording the GABA-activated currents at each membrane potential.

GABA-containing solutions were delivered to the chamber through a custom-made gravity-driven flowpipe, the tip of which was placed approximately 50 µm from the cell. Application was triggered by compression of the tubing connected to the flow pipe with a valve controlled by the Pulse-software. In general, GABA was applied for 0.5-1 sec every 30-40 sec. The sampling interval during application was 1 msec. The patch clamp experiments were performed at room temperature (20-22° C.). Currents were measured at the peak of the response and reversal potentials ($V_{rev}$) were read directly from the I-V plots for each cell.

Wild-type and the mutated $GABA_A$ receptors were characterized concerning reversal potentials in different extracellular solution to identify cation—or anion conductance.

The results of this experiment are presented in Table 1, below.

TABLE 1

| $α_2$ sub-unit | $β_3$ subunit | $γ_2$ sub-unit | $V_{rev}$ Na-R [mV ± SEM] | $V_{rev}$ NMDG-R [mV ± SEM] | $V_{rev}$ Gluconate-R [mV ± SEM] | Kd [³H] Muscimol binding nM | Kd [³H] Flumazenil binding nM | [³⁵S] TBPS binding* |
|---|---|---|---|---|---|---|---|---|
| $α_2$ | $β_3$ | $γ_2$ | 1.3 ± 0.7 | 0.8 ± 2.0 | 33.5 ± 2.4 | 54.7 ± 14.7 | 2.4 ± 0.7 | + |
| $α_2$ | $β_3$ DSGEK | $γ_2$ | −2.7 ± 0.6 | −31.4 ± 1.9 | −9.5 ± 0.7 | 38.0 ± 6.0 | 1.8 ± 0.6 | ÷ |
| $α_2$ | $β_3$ DSGEK | $γ_2$ DSGEK | −3.8 ± 1.5 | −35.1 ± 4.3 | ND | ND | ND | ND |

*(+) indicates more and (÷) indicates less than 2.5% binding of the wt receptor

ND = not determined

As shown in Table 1, the shift in reversal potential from Na—R to Gluconate-R indicates chloride conductance for the wild-type receptor, but not for the mutant receptor, whereas the shift in reversal potential from Na—R to NMDG-R indicate cation conductance for the mutant receptor, but not for the wild-type receptor.

No changes are observed for [³H]muscimol- and [³H] flumazenil binding, indicating that the receptor still is a functional $GABA_A$ receptor, whereas binding of the $GABA_A$ channel blocker [³⁵S]TBPS is abolished by the mutation, indicating a modification of the channel.

The invention claimed is:

1. A cation-conducting human gamma aminobutyric acid type A ($GABA_A$) receptor comprising at least one mutated β or θ $GABA_A$ receptor subunit, wherein the at least one mutation is present in the loop bridging its first and its second transmembrane domain (TM1 and TM2).

2. The receptor of claim 1, wherein the mutated $GABA_A$ receptor subunit is a β $GABA_A$ receptor subunit which has been mutated at the partial amino acid sequence represented by the sequence DASAAR (SEQ ID NO:15).

3. The receptor of claim 1, wherein the mutated $GABA_A$ subunit is a β1, β3 and/or β3 $GABA_A$ receptor subunit.

4. The $GABA_A$ receptor of claim 1, wherein the β receptor subunit sequence DASAAR (SEQ ID NO:15) is substituted with the sequence $X^1X^2X^3X^4X^5$ (SEQ ID NO:18);
   wherein
   $X^1$ designates D or E;
   $X^2$ designates S, C or A;
   $X^3$ designates G, A or V;
   $X^4$ designates E or D; and
   $X^5$ designates K or R.

5. The $GABA_A$ receptor of claim 1, wherein the β receptor subunit sequence DASAAR (SEQ ID NO:15) is substituted with the sequence DSGEK (SEQ ID NO:17) or a subsequence thereof.

6. The GABA$_A$ receptor of claim 1, wherein the β receptor subunit sequence DASAAR (SEQ ID NO:15) is substituted with a sequence selected from the sequences GE, SGE, DSGE (SEQ ID NO:55), GEK, SGEK (SEQ ID NO:56), DSGEK (SEQ ID NO:17), DS, DSG, EK, and GEK.

7. A method of screening a chemical compound for inhibiting or activating the activity of a cation-conducting gamma aminobutyric acid type A (GABA$_A$) receptor comprising at least one mutated β or θ GABA$_A$ receptor subunit, wherein the at least one mutation is present in the loop bridging its first and its second transmembrane domain (TM1 and TM2), which method comprises the steps of:
  (i) contacting a cell comprising the cation-conducting GABA$_A$ receptor with the chemical compound to be screened; and
  (ii) monitoring ion flux through the cation-conducting GABA$_A$ receptor, either directly or indirectly, and thereby determining whether the chemical compound inhibits or activates the activity of the cation-conducting GABA$_A$ receptor.

8. The method according to claim 7, wherein the cell is selected from the group consisting of: a HEK293 cell, a CHO-k1 cell, a BHK cell, a COS7 cell, a PC12 cell, a HiB5 cell, a RN33b cell, and a *Xenopus laevis* oocyte (XLO).

9. The method of either of claims 7-8, wherein monitoring of the ion flux of the cation-conducting GABA$_A$ receptor is performed using fluorescence or radio-ligand methods.

10. The method of claim 7, wherein the cation-conducting GABA$_A$ receptor-containing cell is loaded or incubated with a fluorescence indicator or a radio-ligand that allows for a determination of changes in ion flux through the cation-conducting GABA$_A$ receptor.

11. The method of claim 10, wherein the fluorescence indicator is FLUO-3, FLUO-4, Calcium Green, FURA-2, SBFI, PBFI, CD222, BCECF, DIBAC$_4$(3), DiOC5(3) or DiOC2(3).

12. The method of claim 10, wherein the radio-ligand is Rb$^+$ or an organic cation.

13. The method of claim 7, wherein monitoring of the ion flux of the cation-conducting GABA$_A$ receptor is performed by spectroscopic methods.

14. The method of claim 7, wherein monitoring of the ion flux of the cation-conducting GABA$_A$ receptor is performed by patch clamp techniques.

* * * * *

SEQUENCE LISTING

<160> NUMBER OF SEQ ID NOS: 56

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 1
agtaagcttc tggcttaaca gagaatctgt ggagcgtacg gtgtttggag tcaccactgt     60
cctgac                                                               66

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 2
agtaagcttc tggcttaaca gagactccgg cgagaagact gtgtttggag tcaccactgt     60
cctgac                                                               66

<210> SEQ ID NO 3
<211> LENGTH: 62
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 3
ccaccttagg gagagaattc cgagcactga tgcttagagt tgtcattgtc aggacagtgg     60
tg                                                                   62

<210> SEQ ID NO 4
<211> LENGTH: 66
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 4
ggtaagcttc tggatcaatt atgatgcatc tgaacgcgtt gccctcggga tcaccactgt     60
cctgac                                                               66

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 5
gtaagcttct ggatcaatta tgactccggc gagaaggttg ccctcgggat caccactgtc     60
ctgac                                                                65

<210> SEQ ID NO 6
<211> LENGTH: 62
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 6
ggaccttagg caaggtctcc cgaaggtggg tgttgatggt tgtcattgtc aggacagtgg     60
tg                                                                   62

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 7
ggtaagcttc tggatcaata aggatgctgt tgagcgtacg tctttaggta tcaccactgt     60
cctgac                                                               66

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 8
ggtaagcttc tggatcaata aggactccgg cgagaagaca tctttaggta tcaccactgt     60
cctgac                                                               66

<210> SEQ ID NO 9
<211> LENGTH: 62
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 9
agaccttagg gagcgatttc cgggcaatgg tgctgagggt ggtcattgtc aggacagtgg     60
tg                                                                   62

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 10
gactcgggcg agagagttgc cctcgggatc                                     30

<210> SEQ ID NO 11
<211> LENGTH: 34
<212> TYPE: DNA
<213> ORGANISM: Artificial Sequence
<220> FEATURE:

<223> OTHER INFORMATION: Description of Artificial Sequence: PCR primer
      sequence

<400> SEQUENCE: 11
ctggatcaat tatgacgcag gcgagaaggt tgcc                                    34

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 12
ctggatcaat tatgacgcag gcgagagagt tgccctcggg atc                          43

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: PCR primer
      sequence

<400> SEQUENCE: 13
gagaccttgc ctaagatccc ctatgtcaaa gcc                                     33

<210> SEQ ID NO 14
<211> LENGTH: 6
<212> TYPE: PRT
<213> ORGANISM: Artificial Sequence
<220> FEATURE:
<223> OTHER INFORMATION: Wild-type GABAa receptor alpha subunits

<400> SEQUENCE: 14

Glu Ser Val Pro Ala Arg
1               5

<210> SEQ ID NO 15
<211> LENGTH: 6
<212> TYPE: PRT
<213> ORGANISM: Artificial Sequence
<220> FEATURE:
<223> OTHER INFORMATION: Wild-type GABAA receptor beta subunits

<400> SEQUENCE: 15

Asp Ala Ser Ala Ala Arg
1               5

<210> SEQ ID NO 16
<211> LENGTH: 6
<212> TYPE: PRT
<213> ORGANISM: Artificial Sequence
<220> FEATURE:
<223> OTHER INFORMATION: Wild-type GABAA receptor gamma subunits

<400> SEQUENCE: 16

Asp Ala Val Pro Ala Arg
1               5

<210> SEQ ID NO 17
<211> LENGTH: 5
<212> TYPE: PRT
<213> ORGANISM: Artificial Sequence
<220> FEATURE:
<223> OTHER INFORMATION: Sequence in the loop bridging its first

```
      and its second transmembrane domain (TM1 and TM2)

<400> SEQUENCE: 17

Asp Ser Gly Glu Lys
1               5

<210> SEQ ID NO 18
<211> LENGTH: 5
<212> TYPE: PRT
<213> ORGANISM: Artificial Sequence
<220> FEATURE:
<223> OTHER INFORMATION: Sequence in the loop bridging its first
      and its second transmembrane domain (TM1 and TM2)
<220> FEATURE:
<221> NAME/KEY: misc_feature
<222> LOCATION: (1)..(1)
<223> OTHER INFORMATION: Xaa is Asp or Glu
<220> FEATURE:
<221> NAME/KEY: misc_feature
<222> LOCATION: (2)..(2)
<223> OTHER INFORMATION: Xaa is Ser, Cys or Ala
<220> FEATURE:
<221> NAME/KEY: misc_feature
<222> LOCATION: (3)..(3)
<223> OTHER INFORMATION: Xaa is Gly, Ala or Val
<220> FEATURE:
<221> NAME/KEY: misc_feature
<222> LOCATION: (4)..(4)
<223> OTHER INFORMATION: Xaa is Glu or Asp
<220> FEATURE:
<221> NAME/KEY: misc
<222> LOCATION: (5)..(5)
<223> OTHER INFORMATION: Xaa is Lys or Arg

<400> SEQUENCE: 18

Xaa Xaa Xaa Xaa Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 19

Asp Ser Gly Glu Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 20

Asp Ser Gly Asp Lys
1               5

<210> SEQ ID NO 21
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 21

Asp Ser Ala Glu Lys
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 22

Asp Ser Ala Asp Lys
1               5

<210> SEQ ID NO 23
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 23

Asp Ser Val Glu Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 24

Asp Ser Val Asp Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 25

Asp Cys Gly Glu Lys
1               5

<210> SEQ ID NO 26
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 26

Asp Cys Gly Asp Lys
1               5

<210> SEQ ID NO 27
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 27

Asp Cys Ala Glu Lys
1               5
```

```
<210> SEQ ID NO 28
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 28

Asp Cys Ala Asp Lys
1               5

<210> SEQ ID NO 29
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 29

Asp Cys Val Glu Lys
1               5

<210> SEQ ID NO 30
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 30

Asp Cys Val Asp Lys
1               5

<210> SEQ ID NO 31
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 31

Asp Ala Gly Glu Lys
1               5

<210> SEQ ID NO 32
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 32

Asp Ala Gly Asp Lys
1               5

<210> SEQ ID NO 33
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 33

Asp Ala Ala Glu Lys
1               5
```

```
<210> SEQ ID NO 34
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 34

Asp Ala Ala Asp Lys
1               5

<210> SEQ ID NO 35
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 35

Asp Ala Val Glu Lys
1               5

<210> SEQ ID NO 36
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 36

Asp Ala Val Asp Lys
1               5

<210> SEQ ID NO 37
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 37

Asp Ser Gly Glu Arg
1               5

<210> SEQ ID NO 38
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 38

Asp Ser Gly Asp Arg
1               5

<210> SEQ ID NO 39
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 39

Asp Ser Ala Glu Arg
1               5

<210> SEQ ID NO 40
```

```
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 40

Asp Ser Ala Asp Arg
1               5

<210> SEQ ID NO 41
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 41

Asp Ser Val Glu Arg
1               5

<210> SEQ ID NO 42
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 42

Asp Ser Val Asp Arg
1               5

<210> SEQ ID NO 43
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 43

Asp Cys Gly Glu Arg
1               5

<210> SEQ ID NO 44
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 44

Asp Cys Gly Asp Arg
1               5

<210> SEQ ID NO 45
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 45

Asp Cys Ala Glu Arg
1               5

<210> SEQ ID NO 46
<211> LENGTH: 5
```

<212> TYPE: PRT
<213> ORGANISM: Artificial Sequence
<220> FEATURE:
<223> OTHER INFORMATION: Preferred mutant of the invention

<400> SEQUENCE: 46

Asp Cys Ala Asp Arg
1               5

<210> SEQ ID NO 47
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 47

Asp Cys Val Glu Arg
1               5

<210> SEQ ID NO 48
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 48

Asp Cys Val Asp Arg
1               5

<210> SEQ ID NO 49
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 49

Asp Ala Gly Glu Arg
1               5

<210> SEQ ID NO 50
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 50

Asp Ala Gly Asp Arg
1               5

<210> SEQ ID NO 51
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 51

Asp Ala Ala Glu Arg
1               5

<210> SEQ ID NO 52
<211> LENGTH: 5
<212> TYPE: PRT

-continued

```
<213> ORGANISM: Artificial Sequence
<220> FEATURE:
<223> OTHER INFORMATION: Preferred mutant of the invention

<400> SEQUENCE: 52

Asp Ala Ala Asp Arg
1               5

<210> SEQ ID NO 53
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 53

Asp Ala Val Glu Arg
1               5

<210> SEQ ID NO 54
<211> LENGTH: 5
<212> TYPE: PRT
<213> ORGANISM: Artificial Sequence
<220> FEATURE:
<223> OTHER INFORMATION: Preferred mutant of the invention

<400> SEQUENCE: 54

Asp Ala Val Asp Arg
1               5

<210> SEQ ID NO 55
<211> LENGTH: 4
<212> TYPE: PRT
<213> ORGANISM: Artificial Sequence
<220> FEATURE:
<223> OTHER INFORMATION: Sequence claimed in claim 11

<400> SEQUENCE: 55

Asp Ser Gly Glu
1

<210> SEQ ID NO 56
<211> LENGTH: 4
<212> TYPE: PRT
<213> ORGANISM: Artificial Sequence
<220> FEATURE:
<223> OTHER INFORMATION: Sequence claimed in claim 11

<400> SEQUENCE: 56

Ser Gly Glu Lys
1
```